US006372484B1

(12) United States Patent
Ronchi et al.

(10) Patent No.: US 6,372,484 B1
(45) Date of Patent: Apr. 16, 2002

(54) APPARATUS FOR INTEGRATED POLYMERASE CHAIN REACTION AND CAPILLARY ELECTROPHORESIS

(75) Inventors: Miriam Lisa Ronchi, Wilmington, DE (US); David J. Regester, West Grove, PA (US); Robert Kenneth Kobos, Wilmington; Raymond E. Jackson, Jr., Newark, both of DE (US)

(73) Assignee: E.I. duPont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/488,533

(22) Filed: Jan. 21, 2000

Related U.S. Application Data

(60) Provisional application No. 60/117,208, filed on Jan. 25, 1999.

(51) Int. Cl.[7] ............................ C12M 1/40; G01N 27/26
(52) U.S. Cl. ..................... 435/287.2; 435/6; 435/91.2; 435/303.1; 204/453; 204/604
(58) Field of Search ...................... 435/287.2, 4, 288.7, 435/6, 303.1, 91.2; 204/451–455, 601–605

(56) References Cited

U.S. PATENT DOCUMENTS

| | | | |
|---|---|---|---|
| B1 4,683,195 A | | 11/1990 | Mullis et al. |
| B1 4,683,202 A | | 11/1990 | Mullis |
| 5,229,297 A | | 7/1993 | Schnipelsky et al. |
| 5,475,610 A | | 12/1995 | Atwood et al. |
| 5,639,423 A | | 6/1997 | Northrup et al. |
| 5,646,039 A | | 7/1997 | Northrup et al. |
| 5,674,742 A | | 10/1997 | Northrup et al. |
| 5,755,942 A | * | 5/1998 | Zanzucchi et al. |
| 6,126,804 A | * | 10/2000 | Andersen |
| 6,132,580 A | * | 10/2000 | Mathies et al. |

FOREIGN PATENT DOCUMENTS

EP  0 482 721 A2  4/1992

OTHER PUBLICATIONS

A. Woolley and R. Matheis, "Ultra High Speed DNA Fragment Seperations Using Microfabricated Capillary Array Electrophoresis Chips", Proc. Natl. Acad. Sci., vol. 91, Nov. 1994, pp. 11348–11352.

S. Jacobson, and J.M. Ramsey, "Integrated Microdevice for DNA Restriction Fragment Analysis", Anal. Chem. 1996, vol. 68, 1996 pp. 720–723.

A. Woolley, D. Hadley, P. Landre, A. deMello, R. Mathies, and M. Northrup, Functional Integration of PCR Amplification and Capillary Electrophoresis in a Microfabricated DNA Analysis Device, Anal. Chem., vol. 68, 1996, pp. 4081–4086.

(List continued on next page.)

Primary Examiner—William H. Beisner

(57) ABSTRACT

An apparatus is described for performing polymerase chain reaction (PCR) and capillary electrophoresis (CE) within a single, integrated and disposable device. Fluid enters the device via a sample charging port. From the sample charging port, the fluid travels through an inflow channel to the polymerase chain reaction chamber. This chamber is formed at a thin tab extension of a top portion of the device, and is generally defined by a cavity within the thin tab extension. After PCR is performed, the fluid leaves the polymerase chain reaction chamber through an outflow channel into a first sample well. A vent channel is connected to the first sample well for venting the first sample well to ambient atmosphere. The first sample well and a second sample well are in fluid communication by a sample channel. An electrophoresis separation channel is orthogonal to and intersects the sample channel, and has a first and second electrophoresis buffer well at each end. To perform electrophoresis, voltage is applied to the first and second sample well, and is then applied to the first and second electrophoresis buffer well.

39 Claims, 7 Drawing Sheets

OTHER PUBLICATIONS

M. Roberts, J. Rossler, P. Bercier, and H. Girault, "UV Laser Machined Polymer Substrates for the development of Microdignostic Systems", Anal. Chem., vol. 69, 1997, 2035–2042.

R. McCormick, R. Nelson, M. Alsonso–Amigo, D. Benvegnu, and H. Hooper, Microchannel Electrophoretic Separations of DNA in Injection Molded Plastic Substrates:, Anal. Chem., vol. 69, 1997, pp. 2626–2630.

C. Effenhauser, G. Bruin, A. Paulus, and M. Ehrat, "Integrated Capillary Electrophoresis of Flexible Silicone Microdevices: Analysis of DNA Restriction Fragments and Detection of Single DNA Molecules on Microchips", Anal Chem., vol. 69, 1997, pp.3451–3457.

L. Martynova, L. Locasico, M. Gaitan, G. Kramer, R. Christensen, and W. MecCrehan, "Fabrication of Plastic Microfluid Channels by Imprinting Methods", Anal. Chem., vol. 69, 1997, pp. 4793–4789.

L. Waters, S. Jacobson, N. Krouchinina, J. Khandurina, R. Foote, and J. Ramsey, "Microchip Device for cell Lysis, Multiplex PCR Amplification and Electrophoretic Sizing", Anal Chem. vol. 70, pp. 158–162. (Jan. 1998).

* cited by examiner

US 6,372,484 B1

APPARATUS FOR INTEGRATED POLYMERASE CHAIN REACTION AND CAPILLARY ELECTROPHORESIS

The present application claims priority from the filing date of provisional patent application Ser. No. 60/117,208 filed, Jan. 25, 1999, entitled "APPARATUS FOR INTEGRATED POLYMERASE CHAIN REACTION AND CAPILLARY ELECTROPHORESIS".

The U.S. Government reserves the right to a license for this invention as provided for by the terms of Contract/Grant 70NANB5H1039 sponsored by the Advanced Technology Program (ATP) and administered by the National Institute of Standards and Technology (NIST).

FIELD OF INVENTION

The present invention relates to an apparatus for performing bio-assays and more particularly to a disposable structure for performing polymerase chain reaction (PCR) and capillary electrophoresis (CE) in a protocol for specific bacterial detection and/or identification.

BACKGROUND OF THE INVENTION

The presence of certain suspected spoilage organisms, pathogens, beneficial organisms, or any bacterium in a sample can be detected by performing nucleic acid (DNA) analysis. Different types of organisms have different DNA sequences, which are sources of genetic information. In any given sample, the different nucleotide sequences of the organisms present in the mixture form together a large, indistinguishable background of nucleic acid. If a suspected organism is a part of this mixture, a technique can be performed that will exponentially amplify the number of its specific DNA sequences relative to the others in the sample. A second technique can then be used to separate and measure the amount of each of the different substances relative to each other. If one substance is predominant relative to all of the other substances in the sample, the presence of the suspected organism is then confirmed.

DNA sequences are formed as chains, or strands of a double helix, which pair with each other in a very precise way to form complementary sequences. There are four nucleotide bases, or building blocks of DNA, which are: adenine, cytosine, guanine, and thymine, which are represented respectively by: A, C, G, and T. The "A" on one strand will always pair with the "T" on the other, and the "C" will always pair with the "G," such that the strands are complementary. A gene's sequence is the arrangement of these four letters as a sentence, which can be hundreds or thousands of characters long.

Polymerase chain reaction (PCR) is a technique for amplifying, or copying, the "target" DNA sequences of a pre-selected organism in a sample, possibly by a factor of several million. Copying a DNA sequence requires a supply of the four nucleotide bases, "primers," and DNA polymerase. The primers are short sequences of the beginning and ending portions of the two complementary "target" DNA sequences of an organism to be amplified. DNA polymerase is an enzyme that utilizes the primers and the nucleotide bases to form copies.

The first step of PCR is to heat the reaction mixture containing the target DNA, a large excess of primers, the four nucleotide bases, and DNA polymerase, such that the paired strands of all of the DNA in the sample denature, or separate. The single strands are now accessible for the primers. Next, the sample is cooled to allow double-strands to form again. Because of the large excess of primers, the two strands of the unbound, target DNA sequence templates bind to the complementary primers instead of with each other. In the third step, the temperature is adjusted to obtain maximum activity for the DNA polymerase enzyme. For each DNA sequence that is bound to a short primer, the enzyme will extend the primer's sequence by "hooking" letters together to be complementary to the remaining unmarked portions of the single strands, such that the original double helix for the DNA sequence is replicated. In other words, if after the primer, a single strand contains an "A" nucleotide, the enzyme adds a "T" to the end of primer that is bound to the strand. If the strand next contains a "G," the enzyme adds a "C" to the new chain, and so on, until the end of the DNA strand. This process doubles the number of DNA double helix sequences for the "target" organism in the sample. PCR thus allows a tester to multiply unique regions of DNA so that they can be detected in large genomes. The PCR process can be repeated many times within a short period to exponentially amplify the DNA of the "target" organism in the sample.

Capillary electrophoresis (CE) is a technique for detecting whether a unique region of DNA has been amplified in comparison with other DNA in a sample. A measured quantity of the sample is introduced, with pressure or by applying a voltage (electrokinetic injection), into a sieving buffer-filled capillary. A voltage is then applied along the capillary, which causes the components in the sample to begin to move under the influence of the electrical field. Different components will move at different velocities, such that a separation can be made. The separated components then pass through a beam of light. Each component in the sample absorbs light of a given wavelength as it passes through the beam, and in response thereto, emits light of a different wavelength according to the fluorescence of the component. The light emitted by each component in response to the incident light is detected by a fluorometer as a series of peaks. The area of each peak is proportional to the amount of the substance present in the sample. A single dominant peak for a sample that has undergone PCR is indicative that the "target" DNA is present in the sample and was consequently amplified. Capillary electrophoresis is also useful when testing for a series of peaks in order to detect the presence of multiple products. As an example, this technique is used for performing a fingerprinting technology known as random amplified polymorphic DNA ("RAPD").

Polymerase chain reaction and capillary electrophoresis are generally performed separately. PCR is typically performed in a reaction tube, and CE is performed in fused silica capillaries. Recently, it has been found that small samples may be processed in micro-devices, or microchips. It is known to fabricate devices for performing polymerase chain reaction and devices for performing capillary electrophoresis from crystalline semiconductor substrates. An advantage of using crystalline devices is that the construction can be precisely controlled through etching, and crystalline materials can be bonded by fusion at elevated temperatures. However, it is relatively expensive to fabricate PCR or CE devices from crystalline materials. Various fabrication techniques for plastic devices in CE also have been described including laser ablation, injection molding, silicone molding, and imprinting. However, these techniques were described for performing CE only.

Recently, it has been proposed to perform both polymerase chain reaction and capillary electrophoresis using a single, integrated device. The integration of PCR and CE using a single device allows for a substantial increase in operational speed. Because the process inherently involves less manipulation and handling when performed on a single chip, less operator skill is required. As a further benefit, the reduction of handling reduces problems of contamination and error.

There are many difficulties associated with designing a microchip for performing both PCR and CE. The medium selected must allow for the rapid thermal cycling that is required when heating and cooling a chamber for performing PCR. A material that is sufficiently thick to ensure rigidity and provide room for process elements may not facilitate good and rapid heat transfer needed for PCR. In contrast, it is counterproductive to cycle the temperature of the medium used for electrophoresis. The temperature changes to the electrophoresis portion of the device cause bubbles to form in the separation chamber, which can render the results of electrophoresis inconclusive.

In addition, many benefits of integrating PCR and CE into a single device cannot be realized unless the microchip is sufficiently inexpensive so as to be disposable. Further, a disposable PCR/CE system obviates the difficulties encountered in sterilizing the device for subsequent uses. Carry-over of only a few PCR product molecules into a subsequent PCR procedure can lead to the generation of false positive results. However, devices made from crystalline semiconductor substrates, glass, or a hybrid of both semiconductor substrates and glass, are too costly to be disposable.

SUMMARY OF THE INVENTION

In view of the various difficulties associated with performing PCR and CE in the conventional microdevices described above, there is a need for a device and a method for efficiently performing PCR and CE with accurate results, configured for use by an operator having a minimum of operator skill.

In accordance with the present invention, PCR and CE can be performed in a single, integrated apparatus, formed of a polymeric material, that is to be disposed after each use.

The integrated device of the present invention allows for localized heating of a PCR pouch and isolates the PCR pouch from the areas used for performing CE, thereby preventing the formation of bubbles in the solutions used for CE. The PCR pouch is formed by a cavity within a thin tab, surrounded by sealants, which allows for rapid thermal cycling for performing PCR. The device selectively allows or prevents fluid from reaching a first sample well of the CE device, by connecting or disassociating the PCR portion of the device from the CE portion of the device with a removable barrier. A vent channel is connected with the first sample well to allow air to escape.

In accordance with the invention, there is provided an apparatus for performing both polymerase chain reaction and capillary electrophoresis for a single sample in a single, disposable device that is to be discarded after a single use. The apparatus includes a polymerase chain reaction chamber, an electrophoresis channel, and a removable barrier between the polymerase chain reaction chamber and the electrophoresis channel.

In accordance with a further aspect of the present invention, there is provided an apparatus for performing polymerase chain reaction and capillary electrophoresis within a single, integrated and disposable device. The apparatus has a sample charging port by which a sample enters into the device. A polymerase chain reaction chamber is formed in a thin tab extended portion of the device, the chamber being defined by a cavity within the thin tab extension. An inflow channel is in fluid communication between the sample charging port and the polymerase chain reaction chamber. The apparatus also includes a first and a second sample well in fluid communication by a sample channel, and a vent channel for venting the first sample well to ambient atmosphere. An outflow channel is selectively in fluid communication between the polymerase chain reaction chamber and the first sample well. The apparatus also includes an electrophoresis separation channel orthogonal to and intersecting the sample channel, and having a first and second electrophoresis buffer well at each end thereof.

Also in accordance with the present invention, there is provided a method for performing polymerase chain reaction and capillary electrophoresis on a sample in a single, integrated device having a polymerase chain reaction portion and a capillary electrophoresis portion. A sample is injected into a polymerase chain reaction chamber. A removable barrier is adjusted to isolate the polymerase chain reaction chamber from a sample well of the capillary electrophoresis portion. The polymerase chain reaction chamber is alternately heated and cooled by performing thermal cycling. The removable barrier is adjusted to allow fluid communication between the polymerase chain reaction chamber and the first sample well. A voltage is applied across the first sample well and a second sample well in the capillary electrophoresis portion, wherein the first and second sample wells are in fluid communication via a sample channel, and a voltage is applied across first and second electrophoresis buffer wells in the capillary electrophoresis portion, wherein the first and second electrophoresis buffer wells are in fluid communication via an electrophoresis separation channel, which intersects the sample channel.

DETAILED DESCRIPTION OF THE INVENTION

Figure 1:
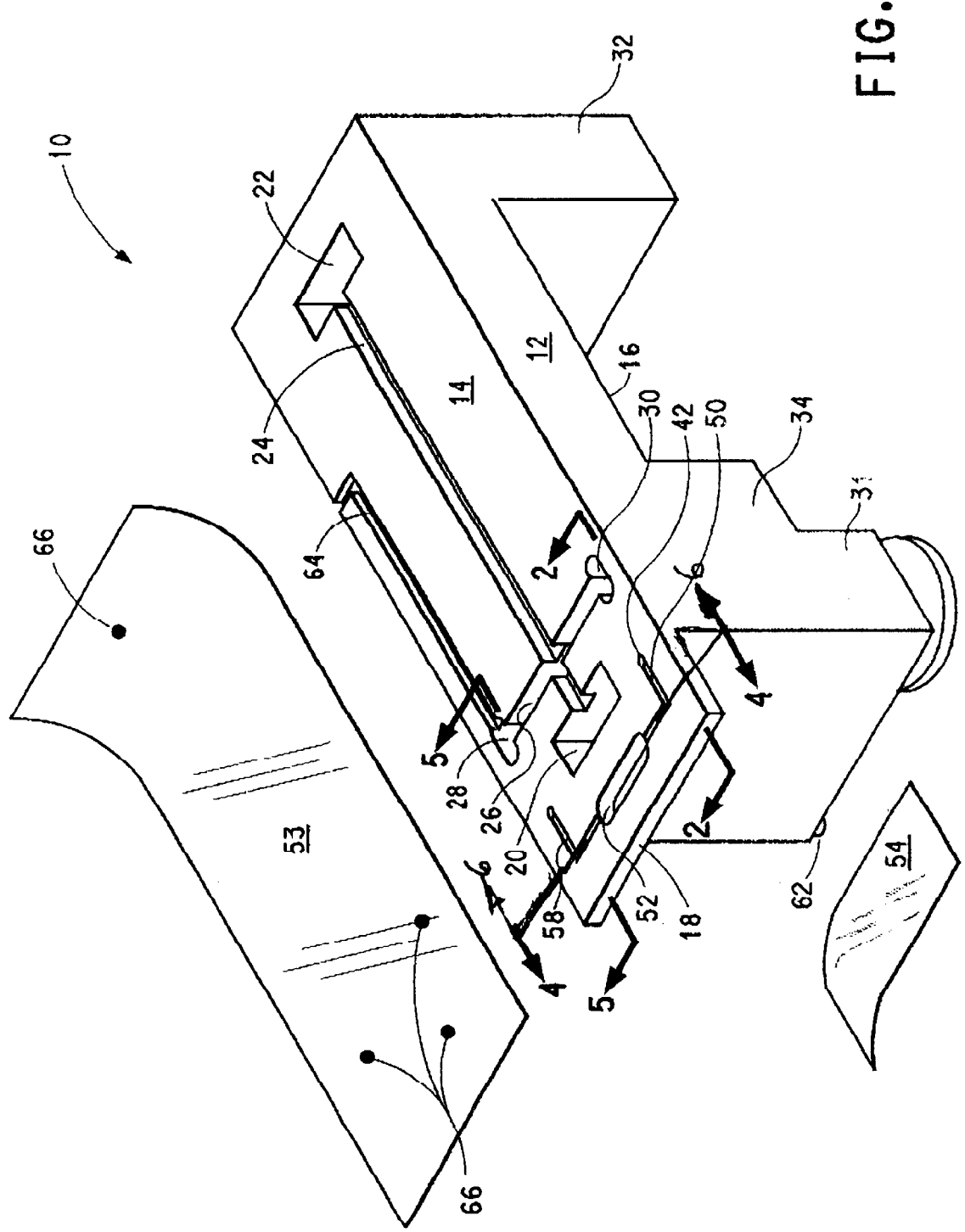
FIG. 1 is a schematic perspective view of an embodiment of the present invention partially sectioned and partially exploded.

Referring to FIG. 1, an embodiment of a combined polymerase chain reaction/capillary electrophoresis (PCR/

CE) apparatus 10 of the present invention is illustrated in a perspective view. Body 12 has opposing planar surfaces 14 and 16 contiguous with legs 31, 32. The legs 31, 32 both span the entire depth of the device, from the front to the back face of the body 12. Leg 31 has an extended portion 34, which has the same depth as leg 31, but does not extend downwardly as far from the lower plane surface 16 as legs 31, 32. Tab 18 is an extension of the horizontal plane surface 14, and is extremely thin as compared with the thickness of the body 12 between surfaces 14, 16.

Figure 5A:
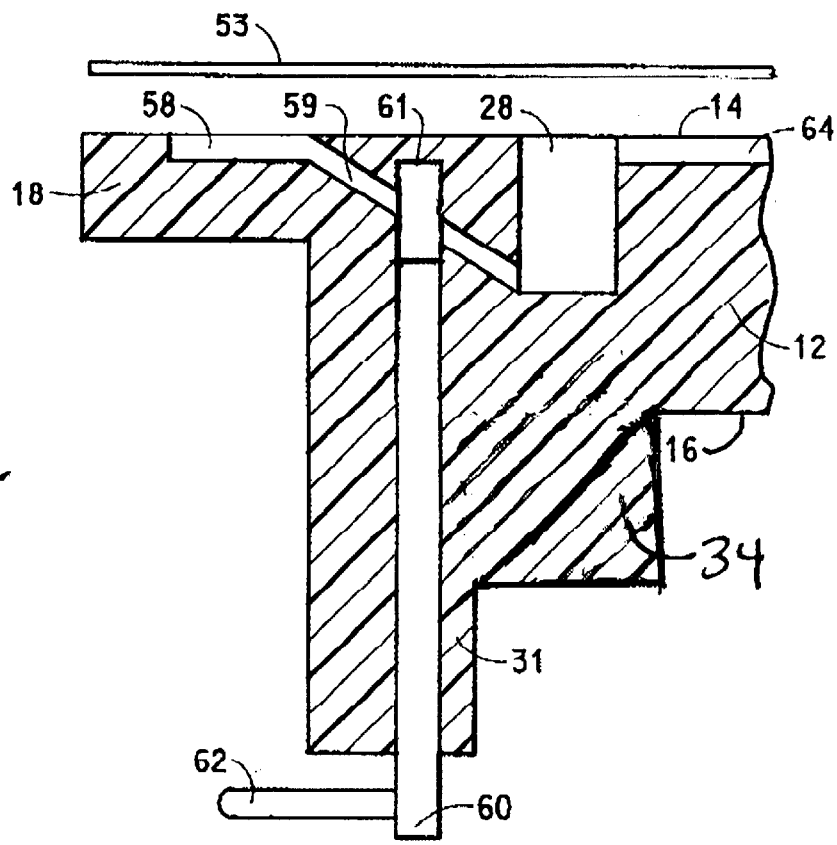
FIG. 5(a) is a sectional view of a valve and one sample well of the embodiment of FIG. 1, from the perspective of the line 5—5 of FIG. 1.
Figure 5B:
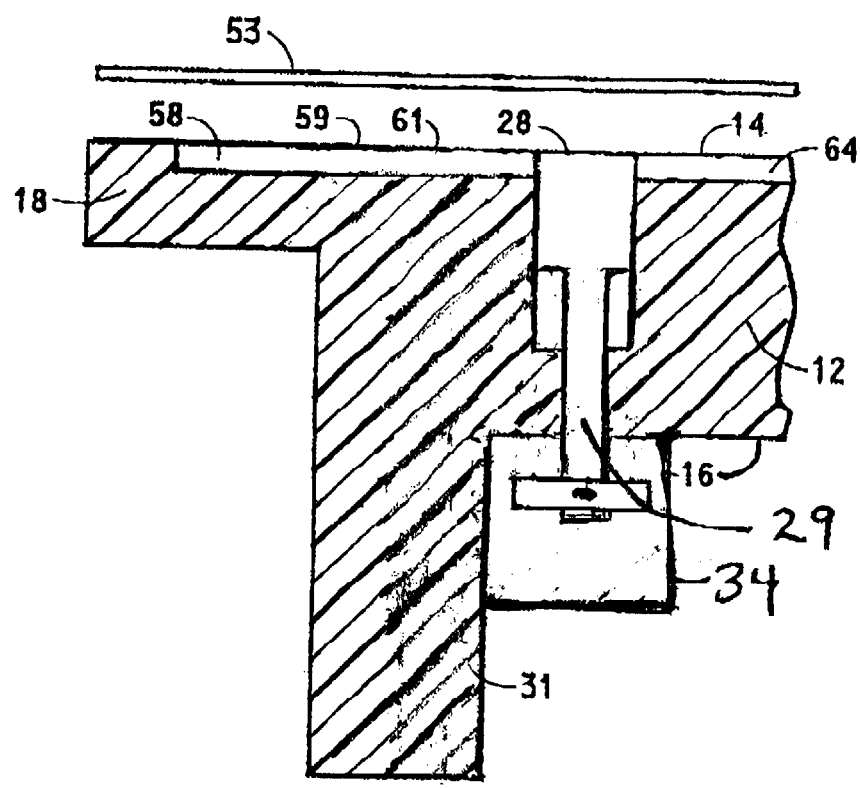
FIG. 5(b) is a sectional view of a stopper and one sample well of an alternative embodiment of the present invention, from the perspective of the line 5—5 of FIG. 1.

A first electrophoresis buffer well 20 and a second electrophoresis buffer well 22 are accessed through surface 14. First and second electrophoresis buffer wells 20, 22 are in fluid communication via electrophoresis channel 24. The first and second electrophoresis buffer wells are blind holes that extend into, but do not penetrate through, legs 31, 32. Near the tab end, electrophoresis channel 24 is crossed at a right angle by sample channel 26, which extends between first sample well 28 and second sample well 30. First sample well 28 and second sample well 30 are blind holes, as shown in FIG. 5($a$).

Figure 2:
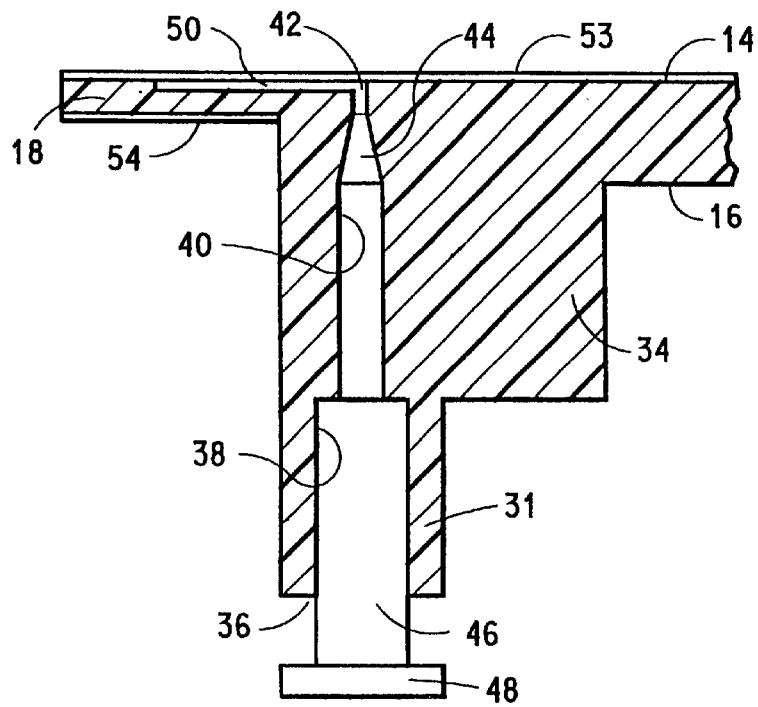
FIG. 2 is an elevational, partial-view of an injection port and piston of the embodiment of FIG. 1, sectioned along the line 2—2 of FIG. 1.

As shown in FIG. 2, a sample charging port 36 is provided through the entire length of leg 31. The charging port comprises three sections 38, 40, and 42, having diameters that proceed from large to small, respectively. Section 42 is connected to section 40 by a tapered section 44. In use, a piston 46 is sized to fit the openings in the sample charging port extending through the sample entry port 36 to the tapered section 44. Piston 46 terminates in a button 48 to facilitate handling during use.

Figure 4:
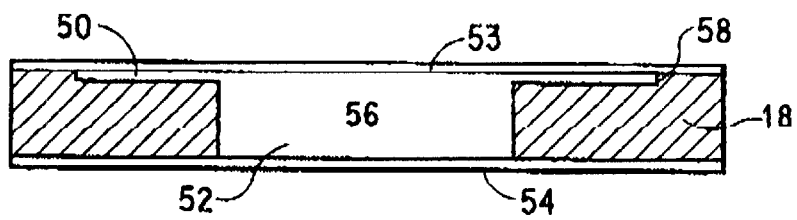
FIG. 4 is a sectional view of the tab end of the embodiment of FIG. 1, from the perspective of the line 4—4 of FIG. 1.

Section 42 is in fluid communication with cavity 52 via inflow channel 50. Cavity 52 can extend entirely through tab 18. The connection between channel 50 and cavity 52 is shown in FIG. 1 as being "L" shaped, but it can also have other configurations. Cavity 52 forms PCR pouch 56, which is defined by the walls of the cavity and two sealants, shown in FIG. 4 as films 53 and 54. Alternatively, cavity 52 can have a thin bottom surface defined by the body, in which case a sealant is only needed on surface 14. In this case, the bottom surface and walls defining the cavity and film 53 together form the PCR pouch, but heat transfer efficiency is reduced due to the additional mass of the bottom surface. Therefore, the PCR pouch is preferably defined by a through cavity and film sealing means.

A suitable material for sealants 53 and 54 is polyester film. These films can be sealed in place by methods known in the art including, but not limited to, local adhesive bonding, heat sealing and pressure sensitive adhesive taping. The adhesive contacts the planar surfaces 14 and 16 to create a seal. Preferably, the adhesive is removed from the portions of the sealant that cover the channels, cavities, wells, and the like. Preferably, the films are pressure sensitive 3M Scotch™ #8540, which is a polyester film with an acrylic adhesive. It is possible that the sealant is removable.

Cavity 52 is connected by way of outflow channel 58 to first sample well 28, as shown in FIG. 5($a$). Outflow channel 58 can have a descending portion 59, drilled or molded into body 12, connected to the bottom of well 28. Valve 60 intercepts descending portion 59, for allowing or preventing fluid flow between cavity 52 and sample well 28. Valve 60 can be cylindrical with cutout portion 61 acting as a quarter-turn valve. Cutout portion 61 of valve 60 can be aligned with descending portion 59 to permit fluid to flow, or can be turned in such a manner to no longer be aligned with descending portion 59 to prevent the flow of fluid. At the other end, valve 60 extends beyond leg 31, and may have a handle 62, as shown in FIG. 5, or a roll pin can be used. The first sample well 28 shown in FIG. 5($a$) is a blind hole in body 12 from surface 14.

Figure 3:
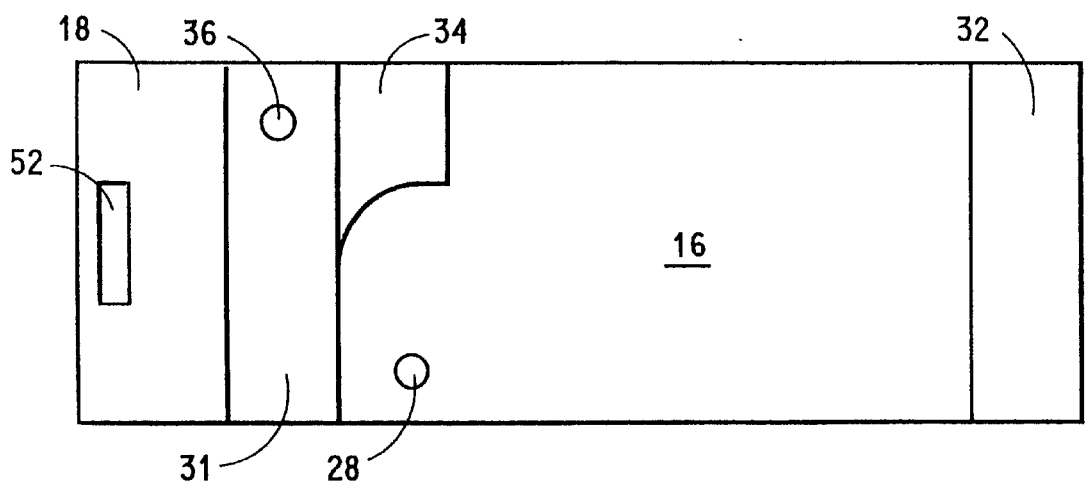
FIG. 3 is a view of the inverted body of an apparatus according to an alternative embodiment of the present invention.

Alternatively, the mechanism for allowing or preventing fluid flow between the PCR pouch and the first sample well can be engageable with the first sample well 28 itself when first sample well 28 is a through hole, as shown in FIG. 3. In this alternative embodiment, a stopper 29 (a roll pin can be used) would be inserted through the lower portion of the sample well 28 to stop the flow of fluid into the well. In this embodiment, surface 16 is contoured to eliminate a rearward portion of abutment 34 to provide for an embodiment wherein the first sample well 28 is a through hole. FIG. 5($b$) shows the side-view of this embodiment. For ease of use for the device, it is preferred to have a blind hole 28, as shown in FIG. 5($a$).

Referring to FIGS. 1 and 5($a$), vent channel 64 is provided along the length of surface 14 from first sample well 28 to the ambient atmosphere. Because fluid enters sample well 28 from the bottom, air is driven upward into vent 64, which minimizes the formation of bubbles.

The body must be fabricated using a material that is compatible with the reagents and thermal conditions of both PCR and CE. Suitable materials include, but are not limited to, polymerics such as polypropylene, polymethylmethacrylate, polyethylene, and polycarbonate. The valve and piston can be machined from inert polymeric material such as TEFLON® fluoropolymer and the like, which has a low coefficient of friction to allow for insertion and rotation. Although injection molding is preferred especially for providing the structural feature of the channels, other micro-fabrication techniques are also suitable, such as machining, stamping, ablation, and electro-forming, as well as any of the rapid prototyping methods emerging into commercialization.

Suitable ranges for the various dimensions of the body 12 include: a length of about 30 to about 100 mm (including the tab extension), a width ranging from about 15 to about 30 mm, a height ranging from about 7 to 12 mm, and a thickness ranging from about 2 to 4 mm. The tab thickness preferably ranges from about 0.25 mm to about 1.27 mm (0.010–0.050 inches). These values for tab thickness yield PCR pouch volumes of about 8.45 $\mu$L to about 42.2 $\mu$L with the preferred volume being about 16.9 $\mu$L. The various channels range from about 1.5 mm to about 0.05 mm wide and from about 0.79 mm to about 0.02 mm deep. The preferable range is from about 0.250 mm to about 0.050 mm wide and from about 0.125 mm to about 0.020 mm deep.

For performing CE, the apparatus of the present invention further includes wires or electrodes to provide a voltage between the first and second sample wells and between the first and second electrophoresis buffer wells. A preferred embodiment is provided by further characterizing film 53 with four electrodes 66, as shown in FIG. 1. Such electrodes can be fabricated by die cutting four holes in film 53 to align with the first and second electrophoresis buffer wells 20 and 22 and first and second sample wells 28 and 30. Thick film silver or platinum paste (available from E.I. du Pont de Nemours and Company, Wilmington, DE) can be used to form electrodes 66. This also can be done by vapor deposition, preferably using platinum. Alternatively, device 10 can be used without such electrodes by inserting wires through film 53, to allow the present invention to be made part of an automatic device. The electrodes also could be built directly into the body 12.

To prepare device 10 for use, body 12 can be washed with methanol, then with water, and charged with an electrophoresis sieving buffer. Hydroxypropylmethyl cellulose (HPMC) in 0.5× Tris-Borate-EDTA (TBE) buffer can be used as the sieving buffer. Other buffer formulations are known to those of skill in the art. The sieving buffer medium is loaded into the first and second electrophoresis buffer wells 20, 22, electrophoresis separation channel 24, second sample well 30 and sample channel 26. Prior to filling the device with a sieving buffer, the valve 60 should be turned to prevent the flow of sieving buffer into the first sample well 28. In an alternative embodiment, a roll pin (not shown) or stopper 29 is inserted into the sample injection well 28 having a through hole, such that the well is completely closed. Sealant films 53 and 54 are sealed in their respective places, as needed to create PCR pouch 56 and contain any material in the wells and channels accessed through surface 14. To best complete filling of the channels, a vacuum can be applied.

Figure 6:
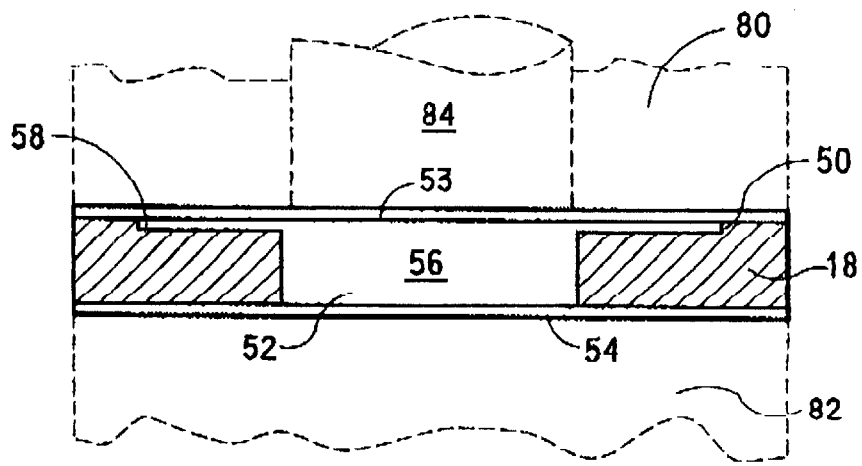
FIG. 6 is a sectional end elevational view of the embodiment of FIG. 1 during thermal cycling, from the perspective of the line 6—6 of FIG. 1.

For use in PCR, the device is inserted such that surface 16 is facing upward, and valve 60 is opened and piston 46 is removed. Liquid analyte is pipetted into sample charging port 36 (see FIG. 2), which substantially fills sections 38 and 40. Piston 46 is replaced and thrust entirely inward, forcing the analyte through section 42 and passage 50 to fill PCR pouch 56. Valve 60 is now closed. The material in PCR pouch 56 is then subjected to thermal cycling by pinching tab 18 between two temperature controlled platens 80 and 82 as shown in FIG. 6.

In the present invention, the mass of the PCR chamber formed by the thin tab is minimal, enabling rapid heat transfer to and from the sample. Moreover, the PCR chamber is positioned at one end of the device isolated from the electrophoresis channel. With the use of a thermocycler designed to heat only the PCR pouch as shown in FIG. 6, the device can be filled with the sieving buffer prior to PCR. The localized heating in combination with the isolated location of the PCR pouch and the poor thermal conductivity of the plastic materials prevents thermal degradation of the sieving polymer or formation of bubbles in the polymer solution.

Temperature control can be performed by any of the known methods, which includes physically moving the analyte and its container between two temperature controlled zones or, preferably, rapidly changing platen temperature by alternately activating heating and cooling means, such as Peltier heating/cooling device, therein. For example, heating can be performed by resistance electrical heating elements and cooling can be performed by circulation of temperature-controlled fluid through appropriate internal passages. However done, a controlled time cycle is carried out a certain number of times for PCR. When this is finished, the device is inverted once more such that surface 14 is facing upward, and valve 60 is then opened. Fluid in PCR pouch 56 is expressed out through passage 58 by squeezing film 53 towards film 54, which is supported by platen 82. This can be done, for example, by a plunger 84 as shown in FIG. 6, or by simply pressing film 53 with a finger. This allows the transfer of fluid from PCR pouch 56 to sample well 28. For use in CE, an electrokinetic injection is used to transfer the DNA from the sample well to the separation channel. Valve 60 is closed and the electrodes 66 in the first and second sample wells 28 and 30 are energized (by means not shown) at an appropriate voltage and with the polarity selected to drive the DNA molecules in the first sample well 28 toward the second sample well 30, as shown in FIG. 1. This places the sample at the intersection of the sample channel 26 and the electrophoresis separation channel 24. The electrodes in the first and second electrophoresis buffer wells 20 and 22 are then energized (by means not shown) at an appropriate voltage and with the polarity selected to drive the DNA molecules at the intersection of electrophoresis separation channel 24 and sample channel 26 toward the second electrophoresis buffer well 22. This separates the fragments into bands.

Fluorescence detection can be performed continuously with a detector, not shown, positioned over the electrophoresis channel 24. The distance from the intersection of electrophoresis separation channel 24 and sample channel 26 to the detector can be optimized to give the desired separation. An intercalating dye, such as SYBR-Green (from Molecular Probes, Inc., Eugene, Oreg.) or ethidium bromide, can be added to the separation medium to provide the fluorescence signal.

The combined PCR/CE device of the present invention can be used and then disposed. Because the device is disposable, this significantly reduces risks of contamination and eliminates the burden of sterilizing the device.

Specific examples of assays performed in the present invention are provided below. The two major functions, PCR and CE, were evaluated individually and then the integrated device was evaluated in a combined PCR and CE process.

EXAMPLE 1

POLYMERASE CHAIN REACTION

An integrated device machined from polypropylene was used. The dimensions of the device were.

overall length=81.3 mm (3.2 inches);
width=25.4 mm (1.00 inches);
length of tab 18=9.5 mm (0.37 inches);
thickness of tab 18=0.5 mm (0.020 inches);
thickness of body 12=3.18 mm (0.125 inches); and
channels=0.250 mm wide×0.125 mm deep.
Platinum wires were used for the electrodes.

A PCR pouch 0.50 mm deep, holding approximately 20 μL, was formed by placing a layer of tape (Scotch™ #850 available from 3M) on each side of the extension tab covering an oval-shaped through cavity. The tape completely covered surface 14. The tape was chosen from a number of different tapes tested because of its adhesive properties and its compatibility with PCR. PCR was evaluated using the Bax™ Screening kits for Salmonella and *E. coli* 0157:H7 (available from Qualicon, Inc., Route 141 and Henry Clay Road, Wilmington, Del.). Tabletted reagents in these kits contain Taq® polymerase (Perkin-Elmer), dNTPs and a target specific primer set for the bacterium of interest. The appropriate tablet was hydrated with PCR reaction buffer containing target DNA ($10^7$ copies). This solution (50 μL) was pipetted into the sample charging port of the integrated device and was transferred into the PCR pouch by inserting a piston into the sample charging port and inserting a roll pin into sample well 28 from surface 16. A portion of the solution was also added to a standard PCR tube and run in another thermal cycler to serve as a control.

The entire device was then placed top side down in a Perkin Elmer Model 9600 Thermocycler for the PCR reaction. An aluminum plate was used to cover the block in the Thermocycler to provide more even heat distribution, and the integrated device was placed on top of the plate with its top side down. An aluminum block was then placed over the PCR pouch to sandwich the pouch between the two aluminum surfaces to ensure good surface contact. To obtain the optimum temperature set points, a thermocouple was placed inside the PCR pouch 56 reaction chamber, and the temperature was monitored during thermal cycling. Once the set points were determined, the thermocouple was used to periodically verify the desired temperatures. The cycling conditions were used: denaturing at 94° C. for 2 min, followed by 35 cycles of 94° C. for 15 sec. and 72° C. for 3 min. A 7 min. elongation at 72° C. completed the reaction.

After the completion of the PCR reaction, a sample was withdrawn from the PCR pouch and electrophoresis was performed on an agarose gel, along with the tube control. The gels were imaged using fluorescence detection with ethidium bromide and a CCD camera detector. Both the tube control and the product from the integrated device showed the expected product band on the gel, confirming that the PCR reaction in the pouch was successful.

EXAMPLE 2

CAPILLARY ELECTROPHORESIS

The polypropylene integrated device of Example 1 was used in this example. The DNA sample was a mass ladder from Gibco BRL which contained DNA fragments of 100, 200, 400, 800, 1200, and 2000 bp. This mass ladder standard was dissolved in PCR buffer to give a total DNA concentration of 10 µg/mL.

Figure 7:
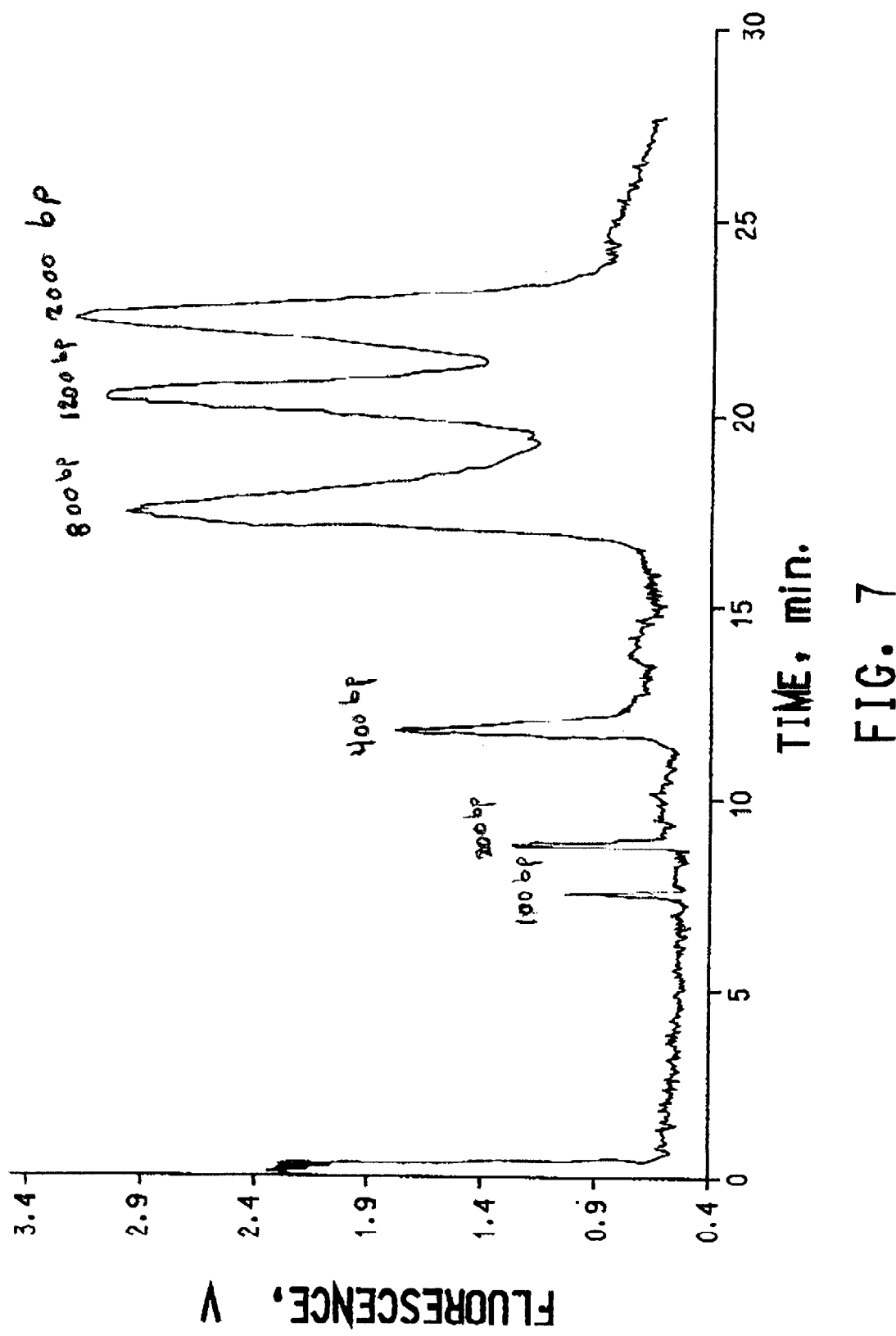
FIG. 7 is an electropherogram using the apparatus of the present invention as described in Example 2.

The channels and the bottom of sample well 28 were covered with tape, Scotch 3M #850, and filled with the sieving buffer, 1.5% hydroxypropylmethyl cellulose (HPMC) in 0.5× TBE buffer containing a 1:1000 dilution of SYBR-Green intercalating dye from Molecular Probes, Inc., Eugene, Oreg. The three top wells (the two sample wells and the first electrophoresis well) were filled with the sieving buffer solution. A vacuum was applied to the far (second) electrophoresis well. The channels were checked under a microscope to ensure that no air bubbles were present. The first sample well was then emptied, removing the sieving buffer, and filled with DNA mass ladder solution. The second electrophoresis well was filled for the first time, and the other wells topped off, with the sieving buffer. Electrodes were placed in the sample wells and the sample was injected into the electrophoresis channel by applying a voltage of 100 V between the two electrodes until fluorescence was observed in the channel intersection with a fluorescence microscope (Olympus Model BX60). Electrodes were also placed in the electrophoresis buffer wells. A fluorescence microscope objective was positioned at a distance 4.5 cm from the sample channel and a voltage of 400 V was applied. The fluorescence signal was recorded using a Lab-View based data collection system. The resulting electropherogram for the mass ladder fragments is shown in FIG. 7, showing DNA fragments of 100, 200, 400, 800, 1200, and 2000 bp corresponding with the DNA sample.

FULLY INTEGRATED PCR/CE RUN

The polypropylene integrated device of Example 1 was used in full for this example. The BAXT™ system positive control (Qualicon, Inc.), which consists of a plasmid and primer that generate an amplicon of 755 bp, was used to test the integrated device in a combined PCR and CE process. The PCR pouch was formed as described in Example 1. Positive control tablets were dissolved in PCR buffer and BSA (bovine serum albumin) and additional plasmid were added. This solution as pipetted into the sample charging port of the inverted integrated device and was transferred to the PCR pouch by inserting a piston into the sample charging port. A portion of the solution was also added to a standard PCR tube and run in another thermal cycler to serve as a control. The integrated device was then placed in a Perkin Elmer Model 9600 thermocycler for the PCR reaction.

Figure 8:
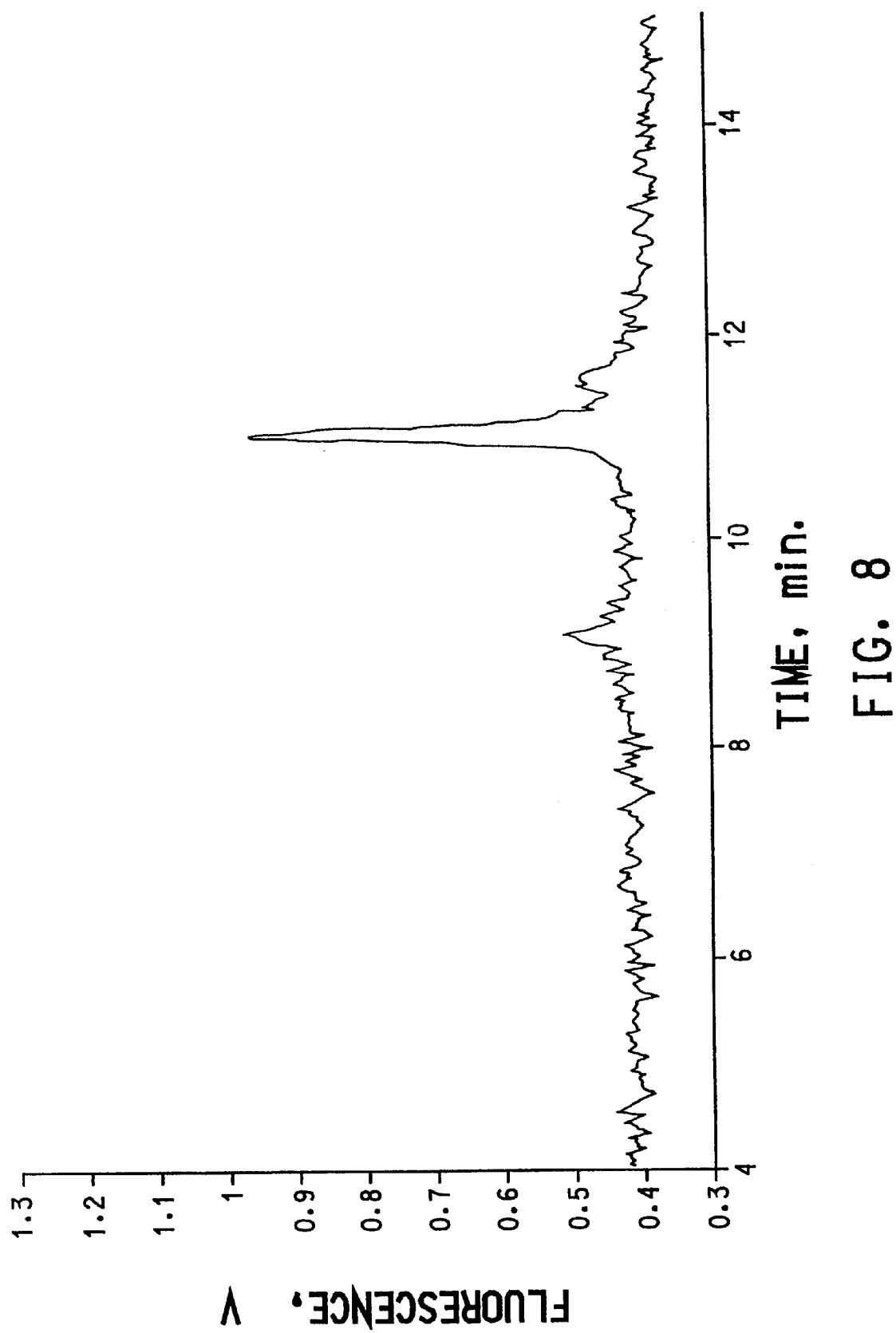
FIG. 8 is an electropherogram showing the results of Example 3.
Figure 9:
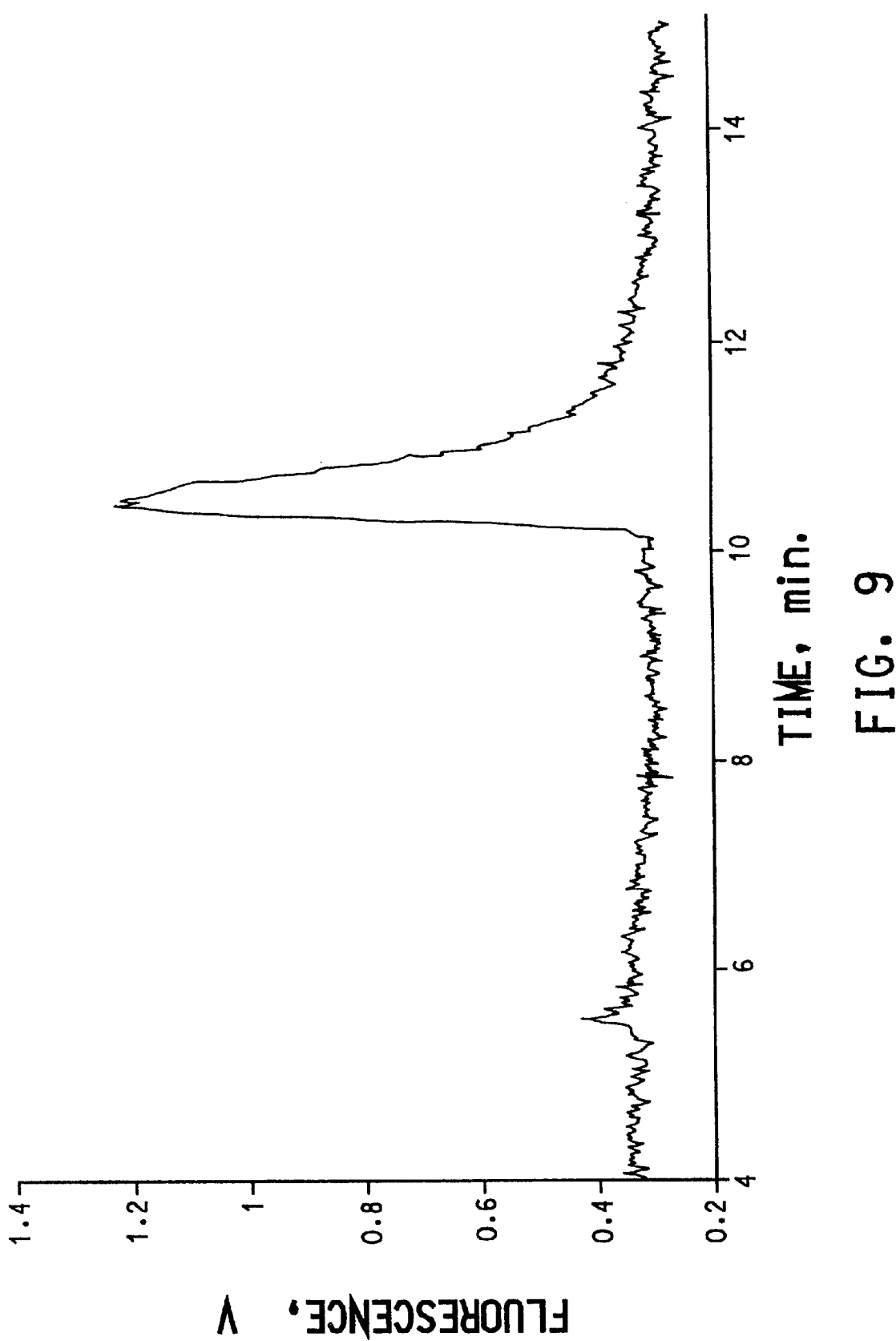
FIG. 9 is an electropherogram showing the results of the control for Example 3.

The device used in this example was not filled with buffer prior to the PCR reaction. After the PCR reaction, the integrated device was removed from the thermocycler, and allowed to cool to room temperature. The roll pin was removed from sample well 28 and the well was covered with tape. The device was inverted so that surface 14 was up. The tape covering all the wells was removed and the electrophoresis channel was filled with sieving buffer, as described in Example 2. The solution was transferred from the PCR pouch to the first sample well by squeezing the pouch. A small amount of deionized water was added to the first sample well because some sample was lost during PCR and the volume was insufficient to allow an electrokinetic injection. The sample was injected into the electrophoresis channel by applying a voltage of 100 V between the first sample well and the second sample well until fluorescence was observed at the intersection of the sample channel and the electrophoresis channel with the fluorescence microscope. The separation was accomplished by applying a voltage of 400 V (73 V/cm) between the first electrophoresis buffer well and the second electrophoresis buffer well, using a separation distance of 4.5 cm. The results are shown in FIG. 8. The BAXT™ system positive control produces a fragment of 755 base pairs, which had a migration time of 11 to 12 minutes at the conditions used. The control, which was run in a conventional PCR tube and detected by CE on a second integrated device of the present invention, is shown in FIG. 9. As can be seen from the data, the results obtained in the integrated run and the control are comparable, demonstrating the success of the integrated run.

EXAMPLE 4

FULLY INTEGRATED PCR/CE RUN WITH LOCALIZED HEATING OF THE PCR POUCH

The polypropylene device of Example 1 is used in full in this example in conjunction with a thermocycler that permits localized heating of the PCR pouch. The BAX™ positive control, which consists of a plasmid and a primer that generate an amplicon of 755 bp, is used to test the integrated process. The PCR pouch and the CE channels are sealed as described in Example 3. The device is then filled with the sieving buffer, as described in Example 3, except that the first sample well is left empty and is sealed by inserting the roll pin or closing the valve. All the wells are then covered with tape, containing preformed electrodes, to completely seal the device. The positive control tablet is dissolved in PCR buffer and BSA and additional plasmid is added. This solution is pipetted into the sample entry port of the inverted integrated device. The sample is transported into the PCR pouch by either removing the roll pin in the first sample well or opening the valve and inserting a piston into the sample entry port. The roll pin is then reinserted, or the valve is closed, to reseal the device. A portion of the solution is also added to a standard PCR tube to serve as the control. The device is then inserted top-side-down into the thermocycler so that the PCR pouch is positioned between the heating plates. In this way, only the PCR pouch is cycled. The cycling conditions are the same as those described in Example 1.

After the PCR reaction, the device is removed from the thermocycler, inverted, and allowed to cool to room temperature. The PCR solution is transferred to the first sample well by removing the roll pin, or opening the valve, and squeezing the pouch. The sample is injected into the electrophoresis separation channel as described in Example 3. The separation is accomplished by applying a voltage 400 V (73 V/cm) between the electrodes so that the DNA fragments migrate toward the far electrophoresis well. The separation distance is 4.5 cm. The fluorescence microscope is used for detection, as described in Example 2.

The electropherogram shows a single peak consistent with that of a 755 bp DNA fragment and with the control, which is run in a second integrated device of the present invention.

The foregoing disclosure of embodiments of the present invention and specific examples illustrating the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only be the claims appended hereto, and by their equivalents.

We claim:

1. An apparatus for performing polymerase chain reaction and capillary electrophoresis within a single, integrated and disposable device, comprising:
   (a) a sample charging port by which a sample enters into the device;
   (b) a polymerase chain reaction chamber formed in a thin tab extended portion of the device, the chamber being defined by a cavity within the thin tab extension;
   (c) an inflow channel in fluid communication between the sample charging port and the polymerase chain reaction chamber;
   (d) a first and a second sample well in fluid communication by a sample channel;
   (e) a vent channel for venting the first sample well to ambient atmosphere;
   (f) an outflow channel selectively in fluid communication between the polymerase chain reaction chamber and the first sample well; and
   (g) an electrophoresis separation channel orthogonal to and intersecting the sample channel, and having a first and second electrophoresis buffer well at each end thereof; and
   (h) electrodes providing contact to fluid to be placed in the first and second sample wells and the first and second buffer wells.

2. The apparatus according to claim 1, further comprising a removable piston for sealing the sample charging port and for injecting fluid from the port into the polymerase chain reaction chamber.

3. The apparatus according to claim 1, wherein the polymerase chain reaction chamber is further defined by at least one sealant for sealing at least one of an upper and lower portion of the thin tab extension.

4. The apparatus according to claim 3, wherein the polymerase chain reaction chamber is further defined by a sealant on each of the upper and lower portions of the thin tab extension.

5. The apparatus according to claim 4, wherein the sealants are removable.

6. The apparatus according to claim 1, further comprising a removable barrier for selectively allowing or preventing fluid to reach the first sample well from the polymerase chain reaction chamber.

7. The apparatus according to claim 6, wherein the removable barrier is a removable valve engageable in a portion of the outflow channel.

8. The apparatus according to claim 6, wherein the removable barrier is a roll pin.

9. The apparatus according to claim 6, wherein the removable barrier is selectively engaged in a through hole in the first sample well to prevent fluid communication between the first sample well and the polymerase chain reaction chamber.

10. The apparatus according to claim 9, wherein the removable barrier is a stopper.

11. The apparatus according to claim 1, wherein the electrical leads are electrodes formed by thick film paste.

12. The apparatus according to claim 1, wherein the electrical leads are wires that penetrate through the sealants.

13. The apparatus according to claim 1, wherein the electrical leads are electrodes that are formed within the apparatus.

14. The apparatus according to claim 1 wherein the device is fabricated from a polymeric material.

15. The apparatus according to claim 14, wherein the polymeric material is selected from the group consisting of polypropylene, polymethyl methacrylate, polyethylene, and polycarbonate.

16. The apparatus according to claim 14, wherein the device is formed by a method selected from the group consisting of molding, machining, stamping, ablation, electro-forming and rapid prototyping.

17. The apparatus according to claim 1, wherein the device is to be discarded after a single use.

18. The apparatus according to claim 1, further comprising electrodes providing contact to fluid to be placed in the first and second sample wells.

19. An apparatus for performing both polymerase chain reaction and capillary electrophoresis for a single sample in a single device comprising:
   a polymerase chain reaction chamber;
   an electrophoresis channel; and
   a removable barrier between the polymerase chain reaction chamber and the electrophoresis channel, wherein the device has a thin tab extension and the polymerase reaction chamber is defined by a cavity within the thin tab extension.

20. The apparatus according to claim 19, further comprising a sample charging port by which a sample enters into the device.

21. The apparatus according to claim 20, further comprising a removable piston for sealing the sample charging port and for injecting fluid from the port into the polymerase chain reaction chamber.

22. The apparatus according to claim 20, further comprising an inflow channel in fluid communication between the sample charging port and the polymerase chain reaction chamber.

23. The apparatus according to claim 20, wherein the polymerase chain reaction chamber is further defined by at least one sealant for sealing at least one of an upper and lower portion of the thin tab extension.

24. The apparatus according to claim 20, wherein the polymerase chain reaction chamber is further defined by a sealant on each of the upper and lower portions of the thin tab extension.

25. The apparatus according to claim 19, further comprising:
   a first and a second sample well in fluid communication via a sample channel;

an outflow channel selectively in fluid communication between the polymerase chain reaction chamber and the first sample well; and a first and a second electrophoresis buffer well at each end of the electrophoresis channel,
wherein the electrophoresis channel is orthogonal to and intersecting the sample channel.

26. The apparatus according to claim 25, further comprising a removable barrier for selectively allowing fluid to reach or preventing fluid from reaching the first sample well from the polymerase chain reaction chamber.

27. The apparatus according to claim 26, wherein the removable barrier is a removable valve engageable in a portion of the outflow channel.

28. The apparatus according to claim 26, wherein the removable barrier is selectively engaged in a through hole in the first sample well to prevent fluid communication between the first sample well and the polymerase chain reaction chamber.

29. The apparatus according to claim 25, further comprising electrodes connected to the first and second sample wells and the first and second electrophoresis buffer wells.

30. The apparatus according to claim 19 wherein the device is fabricated from a polymeric material.

31. The apparatus according to claim 30, wherein the polymeric material is selected from the group consisting of polypropylene, polymethyl methacrylate and polycarbonate.

32. The apparatus according to claim 30, wherein the device is formed by a method selected from the group consisting of molding, machining, stamping, ablation, electro-forming and rapid prototyping.

33. A method for performing polymerase chain reaction and capillary electrophoresis on a sample in the apparatus of claim 19, the method comprising:

injecting the sample into a polymerase chain reaction chamber;

thermal-cycling the sample in the polymerase chain reaction chamber;

directing the sample from the polymerase chain reaction chamber to the capillary electrophoresis channel; and performing electrophoresis on the sample.

34. The method according to claim 33, wherein the sample is directed to the electrophoresis separation channel by applying a voltage across a first sample well and a second sample well in fluid communication via a sample channel that is orthogonal to and intersecting said electrophoresis channel.

35. The method according to claim 33, wherein fluid is directed to the electrophoresis separation channel by application of pressure.

36. An apparatus for performing both polymerase chain reaction and capillary electrophoresis on a sample in a single microfabricated device, comprising a polymerase chain reaction chamber; an electrophoresis channel; a sample charging port through which a sample enters into the device; an inflow channel in fluid communication between the sample charging port and the polymerase chain reaction chamber; a first and a second sample well in fluid communication via a sample channel; a vent channel for venting the first sample well to ambient atmosphere; an outflow channel selectively in fluid communication between the polymerase chain reaction chamber and the first sample well; and a first and second electrophoresis buffer well at each end of the electrophoresis channel, wherein the polymerase chain reaction chamber is formed at a thin tab extension of the device, and the chamber is defined by a cavity within the thin tab extension, and wherein the electrophoresis channel is orthogonal to and intersecting the sample channel.

37. The apparatus according to claim 36, wherein the polymerase chain reaction chamber is further defined by at least one sealant for sealing at least one of an upper and lower portion of the thin tab extension, and the first and second electrophoresis buffer wells and the first and second sample wells are sealed by a sealant.

38. The apparatus according to claim 37 further comprising electrical leads within the sealant that covers the first and second sample wells and the first and second electrophoresis buffer wells.

39. An apparatus for performing both polymerase chain reaction and capillary electrophoresis on a sample in a single microfabricated device, comprising:

a polymerase chain reaction chamber formed at a thin tab extended portion of the device, for facilitating local heating and cooling of the chamber during thermal cycling;

an electrophoresis separation channel having first and second electrophoresis buffer wells on the ends thereof, and being intersected by a sample channel having first and second sample wells on the ends thereof; and a sealant for sealing the sample wells and buffer wells, wherein the sealant further comprises electrical leads contacting each of the sample wells and buffer wells.

* * * * *